(12) United States Patent
Jalgaonkar et al.

(10) Patent No.: US 11,724,069 B2
(45) Date of Patent: Aug. 15, 2023

(54) CATHETER INCLUDING CONTRACTIBLE ELECTROACTIVE ELEMENTS

(71) Applicant: Covidien LP, Mansfield, MA (US)

(72) Inventors: Ujwal Jalgaonkar, Irvine, CA (US);
Edwin Wang, Tustin, CA (US);
Gaurav Girdhar, Ladera Ranch, CA (US)

(73) Assignee: Covidien LP, Mansfield, MA (US)

( * ) Notice: Subject to any disclaimer, the term of this patent is extended or adjusted under 35 U.S.C. 154(b) by 1059 days.

(21) Appl. No.: 16/399,765

(22) Filed: Apr. 30, 2019

(65) Prior Publication Data

US 2020/0345987 A1 Nov. 5, 2020

(51) Int. Cl.
*A61M 25/01* (2006.01)
*A61B 17/00* (2006.01)

(52) U.S. Cl.
CPC ... *A61M 25/0158* (2013.01); *A61B 2017/003* (2013.01); *A61M 2205/0283* (2013.01)

(58) Field of Classification Search
CPC ...... A61M 25/0158; A61M 2205/0283; A61B 2017/003
See application file for complete search history.

(56) References Cited

U.S. PATENT DOCUMENTS

| 4,543,090 A | 9/1985 | McCoy |
| 4,601,283 A | 7/1986 | Chikama |
| 4,753,223 A | 6/1988 | Bremer |
| 5,019,040 A | 5/1991 | Itaoka et al. |
| 5,078,684 A | 1/1992 | Yasuda |
| 5,389,072 A * | 2/1995 | Imran ............... A61B 17/29 60/527 |
| 5,419,767 A | 5/1995 | Eggers et al. |

(Continued)

FOREIGN PATENT DOCUMENTS

| WO | 2013119425 A1 | 8/2013 |
| WO | 2018183832 A1 | 10/2018 |
| WO | 2019147985 A1 | 8/2019 |

OTHER PUBLICATIONS

Tailoring the Response Time of Shape Memory Alloy Wires through Active Cooling and Pre-stress, Journal of Intelligent Material Systems and Structures, vol. 0-2009, published Nov. 5, 2009 (Year: 2009).*

(Continued)

*Primary Examiner* — Laura A Bouchelle
*Assistant Examiner* — John A Doubrava
(74) *Attorney, Agent, or Firm* — Shumaker & Sieffert, P.A.

(57) ABSTRACT

In some examples, a catheter includes an elongated body that includes a proximal portion and a distal portion, and one or more electroactive elements in at least one of the proximal portion or the distal portion of the elongated body. The one or more electroactive elements each include a contractive material configured contract in response to an application of an electrical signal to the respective electroactive element. The contraction of the electroactive elements is configured to change a dimension or a shape of the elongated body. The electroactive elements may be distributed around the elongated body at the distal portion of the elongated body, such as in different axial or radial positions. The electroactive elements may comprise a nickel titanium (NiTi) alloy having a Ni:Ti composition of about 50:50.

24 Claims, 6 Drawing Sheets

(56) References Cited

U.S. PATENT DOCUMENTS

| | | | |
|---|---|---|---|
| 5,531,664 | A | 7/1996 | Adachi et al. |
| 5,810,717 | A | 9/1998 | Maeda et al. |
| 5,997,526 | A | 12/1999 | Giba et al. |
| 6,672,338 | B1 | 1/2004 | Esashi et al. |
| 6,872,433 | B2 | 3/2005 | Seward et al. |
| 6,936,015 | B2 | 8/2005 | Esashi et al. |
| 7,220,269 | B1 | 5/2007 | Ansel et al. |
| 7,976,460 | B2 | 7/2011 | Richardson |
| 8,343,167 | B2 | 1/2013 | Henson |
| 9,078,682 | B2 | 7/2015 | Lenker et al. |
| 9,597,171 | B2 | 3/2017 | Shrivastava et al. |
| 10,350,386 | B2 | 7/2019 | di Palma et al. |
| 10,463,351 | B2 | 11/2019 | Merk et al. |
| 10,624,659 | B2 | 4/2020 | Gamba et al. |
| 2003/0236445 | A1* | 12/2003 | Couvillon, Jr. ......... A61B 5/062 600/114 |
| 2006/0064055 | A1 | 3/2006 | Pile-Spellman et al. |
| 2007/0083084 | A1 | 4/2007 | Esashi et al. |
| 2010/0168667 | A1* | 7/2010 | Kronstedt ......... A61M 25/0147 604/95.05 |
| 2016/0175039 | A1 | 6/2016 | Aujla |
| 2016/0256228 | A1* | 9/2016 | Haartsen ................. A61B 34/30 |
| 2017/0136158 | A1 | 5/2017 | Culhane et al. |
| 2019/0269491 | A1 | 9/2019 | Jalgaonkar et al. |
| 2019/0298396 | A1 | 10/2019 | Gamba et al. |
| 2020/0001046 | A1 | 1/2020 | Yang et al. |

OTHER PUBLICATIONS

International Preliminary Report on Patentability from International Application No. PCT/US2020/028496, dated Nov. 2, 2021, 11 pp.

Komatsubara et al., "Development of the Forward-Looking Active Micro-Catheter Actuated by TI-NI Shape Memory Alloy Springs," 2009 IEEE 22nd International Conference on Micro Electro Mechanical Systems, Jan. 25-29, 2009, IEEE, Mar. 2009, 4 pp.

Namazu et al., "Titanium-Nickel ShapeMemory Alloy Spring Actuator for Forward-Looking Active Catheter," Hindawi Publishing Corporation, Journal. of Metallurgy, vol. 2011, accepted Jan. 9, 2011, 10 pp.

"Introduction to FLEXINOL Actuator Wire," accessed from http://www.dynalloy.com/flexinol.php on or about Mar. 20, 2019, 1 pp.

"Technical Characteristics of Flexinol," Dynalloy, Inc., F1140RevJ, accessed from http://www.dynalloy.com on or about Mar. 20, 2019, 12 pp.

Images Scientific Instruments, "Nitinol/Flexinol Actuator Wire," accessed from https://www.imagesco.com/articles/nitinol/04.html on or about Mar. 20, 2019, 2 pp.

U.S. Appl. No. 17/096,319, filed Nov. 12, 2020, naming inventors Pulugurtha et al.

International Search Report and Written Opinion of International Application No. PCT/US2020/028496, dated Aug. 27, 2020, 18 pp.

\* cited by examiner

CATHETER INCLUDING CONTRACTIBLE ELECTROACTIVE ELEMENTS

TECHNICAL FIELD

This disclosure relates to a medical catheter.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

In some aspects, this disclosure describes example catheters configured change a shape and/or dimensions to steer the catheter (e.g., a distal portion and/or a proximal portion of the catheter) during navigation of the catheter through vasculature of a patient, and/or to configure the catheter for a particular a medical procedure, such as aspiration of a thrombus from the vasculature of the patient.

In examples described herein, a catheter includes electroactive elements configured to, upon the application of electrical energy, curve a portion of the catheter (e.g., a distal tip) and/or stiffen the catheter. One or more electroactive elements may be positioned along a longitudinal axis of the catheter. The electroactive elements may be electrically connected to an electrical conductor that delivers the electrical energy from an energy source. Delivering an electrical signal to an electroactive element on one side of the catheter may cause the electroactive element to contract along the longitudinal axis of the catheter, thereby causing the portion of the catheter to deflect and curve to one side. Delivering electrical signals to electroactive elements on opposite sides of the catheter may cause the electroactive elements to contract along the longitudinal axis on opposite sides of the catheter, thereby keeping the catheter relatively straight while also increasing the stiffness of the catheter. In some examples, the electroactive elements may include a nickel titanium alloy configured to contract in response to a relatively low electrical current. In this way, a catheter may be steered through vasculature of the patient without generating a large amount of heat within the portion of the catheter including the one or more electroactive elements.

In some examples, a catheter includes an elongated body that includes a proximal portion and a distal portion, and one or more electroactive elements at the distal portion of the elongated body. The one or more electroactive elements are each configured to contract in response to an application of an electrical signal to the respective electroactive element. The contraction of the electroactive elements is configured to change at least one of a dimension or a shape of the elongated body. The electroactive elements may be distributed around the elongated body at the distal portion of the elongated body, such as in different axial or radial positions. In some examples, the electroactive elements may comprise electroactive metal alloys such as a nickel titanium (NiTi) alloy having a Ni:Ti composition of about 50:50; piezoelectric elements such as piezoelectric crystals or ceramics; electroactive polymers such as polyvinylidene fluoride (PVDF); or thermoelectric elements exhibiting the Peltier effect or Seebeck effect.

Clause 1: In one example, a catheter comprises an elongated body including a proximal portion and a distal portion; and one or more electroactive elements in at least one of the proximal portion or the distal portion of the elongated body, the one or more electroactive elements each comprising a contractive material configured to contract in response to an application of an electrical signal to the respective electroactive element, the contraction of the contractive material of the one or more electroactive elements being configured to change a dimension or a shape of the elongated body.

Clause 2: In some examples of the catheter of clause 1, the one or more electroactive elements are disposed at a distal tip of the catheter, the distal tip being at a distal end of the distal portion.

Clause 3: In some examples of the catheter of clause 2, the one or more electroactive elements are disposed about 2 centimeters or less from the distal tip of the catheter.

Clause 4: In some examples of the catheter of any of clauses 1-3, the one or more electroactive elements are staggered around the elongated body in a direction orthogonal to a longitudinal axis of the elongated body.

Clause 5: In some examples of the catheter of any of clauses 1-4, the one or more electroactive elements are staggered along a longitudinal axis of the elongated body.

Clause 6: In some examples of the catheter of any of clauses 1-5, the one or more electroactive elements are in a spiral arrangement around the elongated body and along a longitudinal axis of the elongated body.

Clause 7: In some examples of the catheter of any of clauses 1-6, the elongated body further comprises: an inner liner; an outer jacket; and a structural support member positioned between at least a portion of the inner liner and at least a portion of the outer jacket.

Clause 8: In some examples of the catheter of clause 7, at least one of the one or more electroactive elements is in thermal contact with at least a portion of the structural support member.

Clause 9: In some examples of the catheter of clause 8, the structural support member is a coiled structural support member.

Clause 10: In some examples of the catheter of clause 9, the one or more electroactive elements are configured to reduce a coil pitch of the coiled structural support member in response to the application of the electrical signal.

Clause 11: In some examples of the catheter of clause 9 or 10, the one or more electroactive elements are distributed between turns of the coiled structural support member.

Clause 12: In some examples of the catheter of any of clauses 1-11, the one or more electroactive elements comprise at least two electroactive elements that are substantially diametrically opposed.

Clause 13: In some examples of the catheter of any of clauses 1-12, each of the one or more electroactive elements is configured to contract between about 2% and about 8% when heated above a transition temperature of the respective electroactive element.

Clause 14: In some examples of the catheter of any of clauses 1-12, each of the one or more electroactive elements is configured to contract between about 2% and about 8% along a longitudinal axis of the catheter.

Clause 15: In some examples of the catheter of any of clauses 1-14, wherein the contractive material comprises a nickel titanium (NiTi) alloy having a Ni:Ti composition range between about 40:60 and about 60:40.

Clause 16: In some examples of the catheter of clause 15, the nickel titanium alloy comprises a Ni:Ti composition of about 50:50.

Clause 17: In some examples of the catheter of any of clauses 1-16, the one or more electroactive elements have an electrical resistivity greater than about 30 micro-ohms·centimeter.

Clause 18: In some examples of the catheter of any of clauses 1-17, the elongated body comprises one or more electrical conductors electrically coupled to the one or more electroactive elements, the one or more electroactive elements being configured to receive the electrical signal via an electrical conductor of the one or more electrical conductors.

Clause 19: In some examples of the catheter of any of clauses 1-18, wherein a first electroactive element of the one or more electroactive elements is configured to contract, in response to receiving the electrical signal, and bend the at least one of the proximal portion or the distal portion of the elongated body in a first direction away from a longitudinal axis of the elongated body.

Clause 20: In some examples of the catheter of any of clauses 1-19, wherein a first electroactive element and a second electroactive element of the one or more electroactive elements are configured to contract, in response to receiving the electrical signal, and stiffen the at least one of the proximal portion or the distal portion of the elongated body.

Clause 21: In some examples of the catheter of any of clauses 1-20, the elongated body further comprises an expandable structure, the elongated body defining a lumen in fluid communication with the expandable structure, the lumen terminating in a discharge opening, wherein at least one of the one or more electroactive elements is coupled to a plug and is configured to retract the plug relative to a distal end of the elongated body to seal the discharge opening in response to the application of the electrical signal.

Clause 22: In one example, a method comprises receiving, by a control circuitry and from a user interface, a user selection of a particular dimension or shape of an elongated body of a catheter, the catheter comprising one or more electroactive elements in at least one of a proximal portion or a distal portion of the elongated body, the one or more electroactive elements each being configured contract in response to an application of an electrical signal to the respective electroactive element, the contraction of the one or more electroactive elements being configured to change a dimension or a shape of the elongated body; and controlling, by the control circuitry and in response to receiving the user selection, an electrical signal generation circuitry to send a control signal comprising one or more electrical signals to at least one of the one or more electroactive elements to contract the one or more electroactive elements to form the particular dimension or shape of the elongated body.

Clause 23: In some examples of the method of clause 22, the one or more electroactive elements comprise a first electroactive element, and controlling the electrical signal generation circuitry to send a control signal comprises controlling the electrical signal generation circuitry to send an electrical signal to the first electroactive element to contract the first electroactive element and bend the at least one of the proximal portion or the distal portion of the elongated body in a first direction away from a longitudinal axis of the elongated body.

Clause 24: In some examples of the method of clause 22 or clause 23, the one or more electroactive elements comprise at least two electroactive elements that are substantially diametrically opposed, and controlling the electrical signal generation circuitry to send a control signal comprises controlling the electrical signal generation circuitry to send an electrical signal to the at least two electroactive elements to contract the at least two electroactive elements along a longitudinal axis of the elongated body, wherein contraction of the at least two electroactive elements increases a stiffness of the elongated body.

Clause 25: In some examples of the method of any of clauses 22-24, the one or more electroactive elements comprise at least two electroactive elements that are substantially diametrically opposed, and controlling the electrical signal generation circuitry to send a control signal comprises controlling the electrical signal generation circuitry to send an electrical signal to either of the at least two electroactive elements to bend the distal portion of the elongated body in a first direction away from a longitudinal axis of the elongated body.

Clause 26: In some examples of the method of any of clauses 22-25, each electrical signal of the one or more electrical signals has a current less than about 100 milliamps.

Clause 27: In one example, a method comprises inserting a catheter into vasculature of a patient, the catheter comprising an elongated body including a proximal portion and a distal portion; and one or more electroactive elements in at least one of the proximal portion or the distal portion of the elongated body, the one or more electroactive elements each being configured contract in response to an application of an electrical signal to the respective electroactive element, the contraction of the one or more electroactive elements being configured to change a dimension or a shape of the elongated body; and sending the electrical signal to at least one of the one or more electroactive elements to contract the one or more electroactive elements.

Clause 28: In some examples of the method of clause 27, the one or more electroactive elements comprise a first electroactive element, and the electric signal is applied to the first electroactive element to contract the first electroactive element and bend the distal portion of the elongated body in a first direction away from a longitudinal axis of the elongated body.

Clause 29: In some examples of the method of clause 27 or clause 28, the one or more electroactive elements comprise at least two electroactive elements that are substantially diametrically opposed, and the electrical signal is applied to the at least two electroactive elements to contract the at least two electroactive elements along a longitudinal axis of the elongated body.

Clause 30: In some examples of the method of any of clauses 27-29, the one or more electroactive elements comprise at least two electroactive elements that are substantially diametrically opposed, and the electrical signal is applied to either of the at least two electroactive elements to bend the distal portion of the elongated body in a first direction away from a longitudinal axis of the elongated body.

Clause 31: In some examples of the method of any of clauses 27-30, the electrical signal has a current less than about 100 milliamps.

Clause 32: In one example, a catheter comprises an elongated body including a proximal portion and a distal portion; and one or more electroactive elements in at least one of the proximal portion or the distal portion of the elongated body, the one or more electroactive elements each being configured contract in response to an application of an electrical signal to the respective electroactive element, the contraction of the one or more electroactive elements being configured to change a dimension or a shape of the elongated body, the one or more electroactive elements comprising a nickel titanium (NiTi) alloy having a Ni:Ti composition of about 50:50.

Clause 33: In some examples of the catheter of clause 32, the one or more electroactive elements have an electrical resistivity less than about 50 micro-ohms·centimeter.

Clause 34: In some examples of the catheter of clause 32 or 33, the elongated body further comprises one or more electrical conductors electrically coupled to the one or more electroactive elements, the one or more electroactive elements configured to receive the electrical signal via the conductor that configures the one or more electroactive elements to contract along a longitudinal axis of the catheter.

Clause 35: In some examples, a catheter comprises an elongated body defining a lumen terminating in a discharge opening; an expandable structure in fluid communication with the lumen; and an electroactive element coupled to a plug, wherein the electroactive element is configured to retract the plug relative to a distal end of the elongated body to seal the discharge opening in response to an application of an electrical signal to the electroactive element.

The examples described herein may be combined in any permutation or combination.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1A:
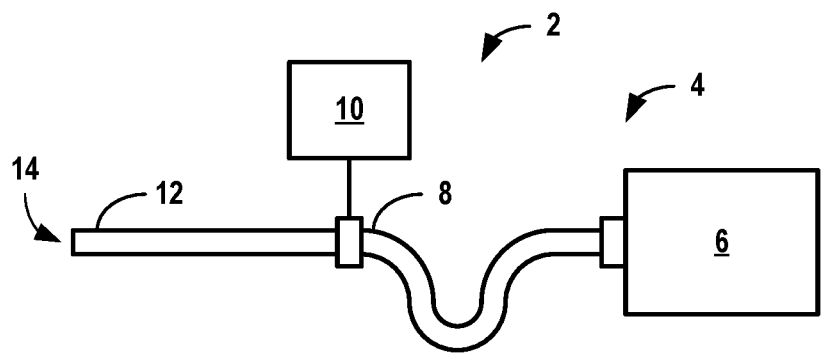
FIG. 1A is a schematic diagram illustrating an example aspiration system that includes a catheter control system and a catheter configured to change a dimension or shape at a portion of the catheter.

The disclosure describes a catheter configured to enable a user to change a shape and/or dimension of the catheter while the catheter is in the vasculature of the patient. For example, with the aid of one or more electroactive elements in an elongated body of the catheter, a clinician may modify a shape or dimension (e.g., to modify a stiffness) of the elongated body to aid navigation of the elongated body through vasculature of a patient, or to better configure the elongated body for a particular a medical procedure, such as aspiration of a thrombus from the vasculature of the patient or inflation of an expandable structure (e.g., a balloon) of the catheter via delivery of a fluid through a lumen of the elongated body.

Catheters may be used to diagnose and treat a variety of conditions, including thrombosis. For example, thrombosis occurs when a thrombus (e.g., a blood clot or other embolus) forms and obstructs vasculature of a patient. To treat a patient with thrombosis, a clinician may position an aspiration catheter in a blood vessel of the patient (i.e., catheterization) near the thrombus, apply suction to the aspiration catheter, and engage the thrombus with a tip of the aspiration catheter. This medical procedure may be, for example, A Direct Aspiration first Pass Technique (ADAPT) for acute stroke thrombectomy, or any other aspiration of thrombus or other material from the neurovasculature or other blood vessels.

To position a catheter in a blood vessel of a patient, a clinician may push a proximal portion (e.g., a proximal end) of the catheter to advance the catheter through the blood vessel. For blood vessels having a relatively straight configuration with high radius bends or few branches, walls of the blood vessel may guide a distal tip of the catheter through the blood vessel. However, some blood vessels, such as cerebral arteries, have tortuous configurations, such that the clinician may use an additional aid, such as a guidewire, a guide catheter, or another guide member, to steer the distal tip of the catheter through the blood vessel. Use of a guide member may add material cost and complexity to the procedure. For example, a clinician may shape the guidewire prior to insertion of the guidewire into the catheter. Vasculature with varying bends may require different shapes, such that the clinician may reshape the guidewire to gain access to different blood vessels. As discussed in further detail below, the catheters described herein that include one or more electroactive elements may enable the catheter to be navigated to a target site within vasculature of a patient without a guide member, e.g., by enabling better control of the shape of the catheter and/or by enabling the catheter to be selectively stiffened to provide better proximal support.

In examples described in this disclosure, a catheter includes one or more electroactive elements positioned in at least one of a proximal portion or a distal portion of an elongated body of the catheter. Each electroactive element is configured to contract in response to application of an electrical signal to the electroactive element. The electroactive elements may be distributed at various locations around the portion of the elongated body, such that selective contraction of one or more electroactive elements changes a shape, dimension, or property of the portion (e.g., a distal tip) of the catheter. For example, asymmetrical contraction of a single electroactive element at a three o'clock position (for an elongated body having a circular cross-section) may guide the distal tip of the catheter to the right, while symmetrical contraction of two electroactive elements at three o'clock and nine o'clock positions may straighten the elongated body within the vasculature and/or increase a rigidity (also referred to herein as a stiffness) of the distal tip of the catheter. In some cases, straightening the elongated body or at least some portions of the catheter using the electroactive elements may facilitate aspiration of material (e.g., thrombus) from the vasculature or delivery of a fluid or medical device to the vasculature by opening up the lumen of the elongated body.

The electroactive elements may be formed from materials, such as nitinol, that contract in response to relatively low levels of current (e.g., 50-100 milliamps (mA)). In this way, the clinician may change the shape, dimension, or property of the portion of the catheter to steer the catheter through vasculature of the patient or to aid a medical procedure without generating a large amount of heat within the portion of the elongated body. A relatively large amount of heat may be undesirable due to the impact of the heat on adjacent tissue and/or on the polymers from which the elongated body of the catheter is formed. For example, a relatively large amount of heat may undesirably heat the one or more polymers from which the elongated body is formed, which may adversely impact the pushability or torqueability of the catheter.

FIG. 1A is a schematic diagram illustrating an example aspiration system 2 that includes a catheter 12 configured to change a dimension or shape at least one portion of catheter 12, which can include, for example, a proximal portion and/or a distal portion. While shown for use with aspiration system 2, catheter 12 may be used for a variety of medical systems in which a clinician may steer a catheter through vasculature of a patient, such as navigation past the aortic arch (e.g., a Type 3 arch), through the proximal internal carotid artery (ICA) segments, or through distal ophthalmic-clinoid segments, thereby minimizing or even avoiding a ledge effect at the ophthalmic or any of the branch vessels emanating from the ICA. In some cases, a ledge effect refers to a distal end of catheter 12 catching on certain anatomical features as it is advanced through vasculature of the patient due to a relatively abrupt transition in cross-sectional dimensions between catheter 12 and an inner guide member (e.g., a microcatheter or a guidewire) that results in the distal end of catheter 12 defining a ledge. In other examples, the catheter may be a relatively low profile (e.g., 0.021 or 0.027 inch diameter) device delivery catheter and actuator for preferential navigation that may help cross a stenotic lesion or a distal aneurysm, which may be challenging with current navigation aids such as guidewires and balloons. Catheter 12 may also reduce a number of devices and steps a practitioner has to take to be able to treat a neurovascular disease.

In addition to catheter 12, aspiration system 2 includes a catheter control system 10 and a fluid handling system 4. Fluid handling system 4 includes an aspiration pump 6 and aspiration tubing 8. Aspiration tubing 8 is coupled to a proximal portion of catheter 12, such that aspiration pump 6 is in fluidic communication with an inner lumen of catheter 12. Fluid handling system 4 is configured to deliver fluid from aspiration pump 6 through a lumen of catheter 12 and receive fluid through the lumen of catheter 12 into aspiration pump 6. Catheter 12 may be used to remove a thrombus, such as a clot or other material such as plaques or foreign bodies, from vasculature of a patient. In such examples, a positive pressure may be applied, such as by aspiration pump 6, to the proximal end of catheter 12 to deliver aspiration fluid to the site of the thrombus and a negative pressure may be applied, such as by aspiration pump 6, to the proximal end of catheter 12 to draw a thrombus into catheter 12 through one or more distal openings at a distal tip 14 of catheter 12.

In some cases, a clinician may steer catheter 12 through the vasculature of a patient by pushing or rotating a hub and/or the proximal portion of catheter 12 to navigate the distal portion of catheter 12 through the vasculature of a patient. For example, the clinician may apply torque to the hub and/or the proximal portion of catheter 12 to rotate the distal portion of catheter 12. As such, catheter 12 may be structurally configured to be relatively flexible, pushable, and relatively kink- and buckle-resistant, so that it may resist buckling when a pushing force is applied to a relatively proximal section of catheter 12 to advance catheter 12 distally through vasculature, and so that it may resist kinking when traversing around a tight turn in the vasculature.

In some examples, catheter 12 is configured to substantially conform to the curvature of the vasculature. In addition, in some examples, catheter 12 may have a column strength and flexibility that allows at least the distal portion of catheter 12 to be navigated from a femoral artery, through the aorta of the patient, and into the intracranial vascular system of the patient, e.g., to reach a relatively distal treatment site. Alternatively, the catheter 12 can have a column strength (and/or be otherwise configured) to allow the distal portion of the catheter 12 to be navigated from a radial artery, through the aorta of the patient or otherwise to a common carotid or vertebral artery, and into the intracranial vascular system of the patient, e.g., to reach a relatively distal treatment site. In some examples, catheter 12 may be a guide catheter that is introduced into the vasculature before another catheter, and may define a pathway through which the other catheter may be navigated to a target treatment site.

In some examples, catheter 12 is configured to access relatively distal locations in a patient including, for example, the middle cerebral artery (MCA), internal carotid artery (ICA), the Circle of Willis, and tissue sites more distal than the MCA, ICA, and the Circle of Willis. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists or turns) through the vasculature to reach these tissue sites. To navigate these tortuous pathways, system 2 may be configured to steer catheter 12 (e.g., distal tip 14 or another portion of catheter 12) through the vasculature by using one or more electroactive elements configured to contract in response to an electrical signal. Although primarily described as being used to reach relatively distal vasculature sites, catheter 12 may also be configured to be used with other target tissue sites. For example, catheter 12 may be used to access tissue sites throughout the coronary and peripheral vasculature, the gastrointestinal tract, the urethra, ureters, fallopian tubes, veins and other body lumens.

Figure 1B:
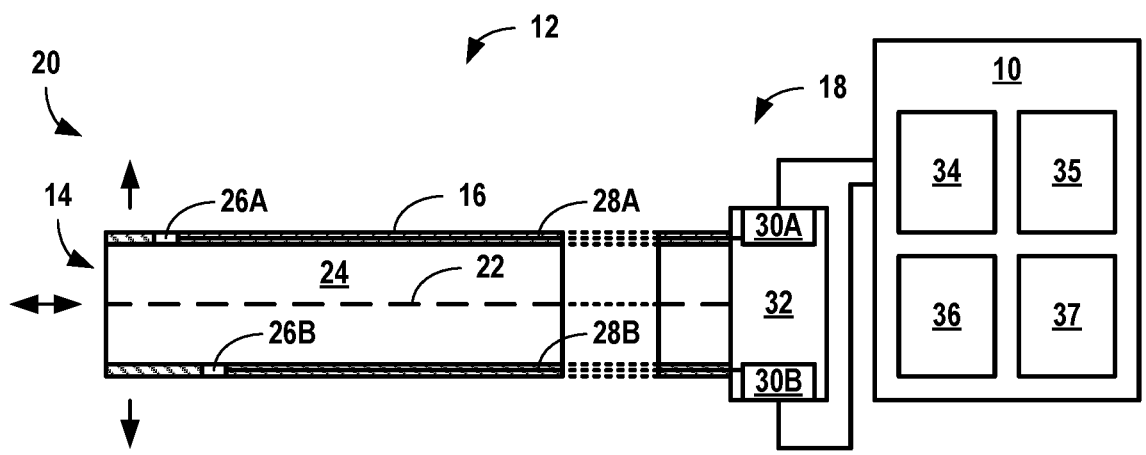
FIG. 1B is a schematic longitudinal cross-sectional diagram illustrating the example catheter and the example catheter control system of FIG. 1A.

FIG. 1B is a schematic longitudinal cross-sectional diagram illustrating example catheter 12 and catheter control system 10 of FIG. 1A. Catheter 12 includes an elongated body 16 and a connection hub 32. Elongated body 16 includes a proximal portion 18 and a distal portion 20. Elongated body 16 may be configured to be advanced through vasculature of a patient via a pushing force applied to proximal portion 18 of elongated body 16 with minimal or no buckling, kinking, or otherwise undesirably deforming (e.g., ovalization). In examples described herein, proximal portion 18 and distal portion 20 of elongated body 16 (or catheter 12) may refer to sections of elongated body 16 that include a proximal end and a distal end, respectively, of elongated body 16. Proximal portion 18 and distal portion 20 may be equal in length in some examples, or may have different lengths in other examples. In some cases, proximal portion 18 and distal portion 20 make up the entire length of elongated body 16, such that proximal portion 18 and distal portion 20 are directly adjacent to each other. In other examples, elongated body 16 may include an intermediate portion that is between proximal portion 18 and distal portion 20.

Elongated body 16 defines an inner lumen 24 and a longitudinal axis 22 extending through elongated body 16. Inner lumen 24 is configured to transport fluid, such as aspiration fluid, blood, and particulates in the fluid, a device, such as another catheter, or a guidewire from distal portion 20 of elongated body 16 to proximal portion 18 of elongated body 16.

In some examples, catheter 12 may be described in terms of a working length of elongated body 16 of catheter 12. The working length of catheter 12 may depend on the location of the target tissue site within the body of a patient or may depend on the medical procedure for which catheter 12 is used. For example, if catheter 12 is a distal access catheter used to access vasculature in a brain of a patient from a femoral artery access point at the groin of the patient, the elongated body of catheter 12 may have a working length of about 115 centimeters (cm) to about 145 cm or more, such as about 130 cm, although other lengths may be used. Distal portion 20 may be about 5 cm to about 35 cm in length. Proximal portion 18 may be about 90 cm to about 130 cm in length, depending on the length of distal portion 20.

In the example shown in FIG. 1B, catheter 12 includes one or more electroactive elements 26 at distal portion 20 of elongated body 16. As discussed above, in other examples, proximal portion 18 (and/or an intermediate portion if present) may include one or more electroactive elements 26 in addition to or instead of distal portion 20. In the example of FIG. 1B, catheter 12 includes a first electroactive element 26A and a second electroactive element 26B (collectively referred to as "electroactive elements 26"). In some examples, electroactive elements 26 are disposed at distal tip 14 of distal portion 20 of elongated body 16, which may enable a clinician to better steer of a lead end of elongated body 16 through vasculature. For example, to guide catheter 12 through vasculature of a patient, a distal tip 14 may be deflected in a clinician-controlled direction via the electroactive elements 26 in the distal tip 14 to steer catheter 12. In some examples, electroactive elements 26 may be disposed less than or equal to about 2 cm (e.g., 2 cm or within 10% of 2 cm) from distal tip 14 of catheter 12. In other examples, electroactive elements 26 may be disposed at other portions of elongated body 16, such as proximal portion 18 or an intermediate portion. For example, an intermediate portion of catheter 12 may include electroactive elements 26 to stiffen the intermediate portion, such as to decrease resistance to fluid flow through catheter 12.

Elongated body 16 includes one or more electrical conductors 28 electrically coupled to one or more electroactive elements 26. For example, electrical conductors 28 may be positioned within a wall of elongated body 16, such as between layers of the elongated body 16 or embedded in a layer of elongated body 16. Each electrical conductor 28 extends about longitudinal axis 22 of the elongated body 16; in other examples, one or more conductors 28 may be helically wound around a central longitudinal axis 22, which may help elongated body 16 maintain a higher degree of flexibility compared to some longitudinal arrangements of conductors 28. The conductor(s) 28 can thus serve both as an electrical conductor to the electroactive element(s) 26 and as a structural support member or structural support coil of the catheter 12 and/or elongated body 16. As an alternative or supplement to a structural support coil, the electrical conductor(s) 28 can form part of a tubular braid that serves as a structural support member of the catheter 12 and/or elongated body 16.

In the example of FIG. 1B, electrical conductor 28A is electrically coupled to electroactive element 26A and electrical conductor 28B is electrically coupled to electroactive element 26B. Electrically connecting electroactive elements 26 to respective electrical conductors 28 may enable more selective delivery of electrical signals to electroactive elements 26, which may enable more fine-tuned modifications to the shape and/or dimensions of catheter 12. However, in other examples, each electrical conductor 28 may be coupled to more than one electroactive element 26 (e.g., a set of electroactive elements 26), such that an electrical signal supplied through an electrical conductor 28 may cause a set of electroactive elements 26 to contract. Electroactive elements 26 may be configured to receive the electrical signal via conductor that configures the one or more electroactive elements 26 to contract along longitudinal axis 22 of catheter 12. While illustrated as a single conductor, each electrical conductor 28 may be configured to create a closed circuit between a respective electroactive element 26 and a source of the electrical signal, such as catheter control system 10. Electroactive elements 26 may be coupled to electroactive conductors 28 by a variety of methods including, but not limited to, soldering, conductive adhesives, mechanical shrinking/embedding within a polymer jacket, or other methods configured to ensure contact between electrical conductors 28 and electroactive elements 26. In some examples, electroactive elements 26 may be coupled to electrical conductors 28 at a distal end of each electroactive element 26.

Connection hub 32 may be configured to couple catheter 12 to catheter control system 10. Connection hub 32 may include one or more connectors 30 electrically coupled to a respective electrical conductor 28 and configured to receive or otherwise electrically connect to one or more output leads of catheter control system 10. In the example of FIG. 1B, connection hub 32 includes connector 30A and 30B (collectively referred to as "connectors 30"). In the example shown in FIG. 1B, connector 30A is electrically coupled to electroactive element 26A through conductor 28A, and connector 30B is electrically coupled to electroactive element 26B through conductor 28B.

Each electroactive element 26 is configured to contract in response to an application of an electrical signal to the respective electroactive element 26. The contraction of one or more electroactive elements 26 is configured to change a dimension or a shape of elongated body 16. As such, a composition, shape, and/or distribution of electroactive elements 26 may be selected and configured to create the change in dimension or shape of elongated body 16 in response to an electrical signal from catheter control system 10. In some examples, a change in dimensions may include a change in longitudinal length greater than about 2% (e.g., 2% to 5% or greater than 5%), such as for electroactive elements 26 that are oriented substantially parallel to longitudinal axis 22 of catheter 12. In some examples, a change in dimensions may include a change in longitudinal length that is less than about 2%, such as for electroactive elements 26 that are not oriented substantially parallel to longitudinal axis 22 of catheter 12. For example, electroactive elements 26 may be in a coiled configuration, such that only a portion of a change in dimension may be parallel to longitudinal axis 22 of catheter 12. As such, an effective change in length of catheter 12 may be configured based on an orientation of electroactive elements 26.

In some examples, electroactive elements 26 are configured to contract along longitudinal axis 22. Longitudinal axis 22 may generally define an orientation of catheter 12 in a direction of advancement of catheter 12. In some examples, each of the one or more electroactive elements 26 is configured to contract between about 2% and about 8% along longitudinal axis 22 of elongated body 16. For example, each electroactive element 26 may contract, after receiving the electrical signal, between about 2% and about 8% along its length (e.g., along longitudinal axis 22 in the case of electroactive elements 26 having a linear configuration) relative to a length of the electroactive element prior to receiving the electrical signal.

In some instances, asymmetrical contraction of electroactive elements 26 may cause deflection of distal tip 14 away from a central longitudinal axis 22 that is defined when elongated body 16 is in a linear configuration. For example, at a particular axial position on elongated body 16, contraction of one or more electroactive elements 26 on a first side of elongated body 16 may be greater than contraction of one or more electroactive elements 26 on a second, opposing side of elongated body 16, such as through application of a higher current electrical signal to electroactive elements 26 on the first side than the second side. As such, the stronger contraction on the first side may cause a portion of elongated body 16 distal to the axial position to bend away from the central longitudinal axis 22 of a more proximal portion of elongated body 16. This bend may have a deflection angle, a radius of curvature, a deflection distance, or other measure of displacement from longitudinal axis 22, as will be described in FIGS. 3A-3E below.

In some instances, symmetrical contraction (e.g. across a plane of symmetry) of symmetrically arranged electroactive elements 26 may cause retraction of distal tip 14 along longitudinal axis 22. For example, at a particular axial position of elongated body 16, contraction of the one or more electroactive elements 26 on the first side of elongated body 16 may be substantially equal to contraction the one or more electroactive elements 26 on the second, opposing side of elongated body 16, such as through application of equal electrical signals to symmetrically positioned electroactive elements 26 on the first and second sides. As such, the substantially equal contraction on the first and second sides may cause a portion of elongated body 16 corresponding to the electroactive elements to retract along longitudinal axis 22. While described above with respect to a single plane of symmetry, in some examples, symmetrical contraction may involve more than one plane of symmetry. For example, equal contraction of electroactive elements 26 distributed at 120 degrees around a circumference of elongated body 16 may retract without significant deflection of elongated body 16 relative to a central longitudinal axis 22.

Electroactive elements 26 can comprise one or more materials that contract and/or elongate (or expand) in response to an applied electrical current. Instead of or in addition to such a property, electroactive elements 26 can comprise one or more materials that convert electrical energy to thermal energy and contract and/or elongate (or expand) in response to receiving or generating thermal energy. For example, electroactive elements 26 may be configured to receive an electrical signal, such as from catheter control system 10, and convert the electrical signal to thermal energy, such as through Joule heating, Peltier effect, or any other mechanism that converts electrical energy to thermal energy. Electroactive elements 26 may be configured to contract and/or elongate (or expand) in response to receiving thermal energy at least partly generated by the electrical energy, such as through phase transition, change in vibrational modes, or any other mechanism that causes a material to contract in response to receiving thermal energy. In some examples, the electroactive elements may comprise electroactive metal alloys such as a nickel titanium (NiTi) alloy having a Ni:Ti composition of about 50:50, or piezoelectric elements such as piezoelectric crystals or ceramics, or electroactive polymers such as polyvinylidene fluoride (PVDF), or thermoelectric elements exhibiting the Peltier effect or Seebeck effect In some examples, electroactive elements 26 comprise one or more materials that resistively heat in response to an electrical signal. For example, electroactive elements 26 may be formed from materials having a relatively high electrical resistivity, such that a relatively high amount of heat is generated by electroactive elements 26 for a particular level of current. In some examples, one or more electroactive elements have an electrical resistivity greater than about 30 micro-ohms·centimeter ($\mu\Omega$·cm) at room temperature. For example, the above-mentioned nickel titanium alloys, such as nitinol and a Ni:Ti composition of about 50:50 (e.g., FLEXINOL), are examples of thermoactive materials that may have a desired resistivity specification.

In some examples, electroactive elements 26 comprise one or more materials having a high degree of negative thermal expansion (a "thermally contractive material") for intended operating conditions of catheter 12. A thermally contractive material may be any material configured to contract in at least one dimension in response to an electrical signal. For example, a thermally contractive material may be selected for a negative coefficient of thermal expansion.

In some examples, electroactive elements 26 may be configured to contract in a direction substantially parallel to longitudinal axis 22, while contracting, expanding, or neither contracting nor expanding in any other direction. For example, the thermally contractive material of electroactive elements 26 may be selected for a negative coefficient of linear thermal expansion. To configure the contraction of the electroactive elements 26 along the longitudinal axis, electroactive elements 26 may be oriented so that a direction of linear thermal contraction is substantially parallel (e.g., parallel to the extent permitted by manufacturing tolerances) to longitudinal axis 22. In this way, electroactive elements 26 may be configured to contract in a direction parallel to longitudinal axis 22. In some examples, electroactive elements 26 may be configured to contract in substantially a single direction.

In some examples, electroactive elements 26 comprise one or more thermally contractive materials that contract when heated above a phase transition temperature ("phase transition materials"). For example, electroactive elements 26 may be at a first, expanded phase below the phase transition temperature and a second, contracted phase above the phase transition temperature. A phase transition material may be selected for a variety of factors including, but not limited to, high electrical resistivity. In some examples, each of the one or more electroactive elements 26 is configured to contract of about 2% to about 8% when heated above a transition temperature of the respective electroactive element. In some examples, electroactive elements 26 may be configured to contract greater than 2% in response to an electrical signal less than about 100 mA.

In some examples, electroactive elements 26 comprise a nickel titanium (NiTi) alloy having a Ni:Ti composition range of 45:55 to about 55:45. For example, the composition range of the nickel titanium alloy may be configured for a particular transition temperature from an expanded martensitic phase to a contracted austenite phase. In some examples, the nickel titanium alloy comprises a Ni:Ti composition of about 50:50 (e.g., FLEXINOL). For example, a 50:50 Ni:Ti composition may have a transition temperature of about 70° C., which may be high enough that electroactive elements 26 do not contract in response to body heat but low enough that a relatively small amount of heat may be used to contract electroactive elements 26. It is believed that for a given electrical signal, electroactive elements 26 formed from a NiTi alloy having a Ni:Ti composition range of 50:50 may contract more than electroactive elements formed from a NiTi alloy having a Ni:Ti composition range of 51:49, as in the case of a more conventional nitinol.

In some examples, electroactive elements 26 comprise one or more materials having a high electroactive effect (a "electroactive material"). An electroactive material may be any material that directly converts electric potential into a substantial temperature difference. An electroactive material may be selected for a variety of properties including, but not limited to, high electrical conductivity, high Seebeck coefficient, low thermal conductivity, and other properties related to electroactive effects (e.g., Seebeck effect, Peltier effect, etc.) of materials.

Electroactive elements 26 may have a variety of shapes. Shapes that may be used for electroactive elements may include, but are not limited to, wires, cylinders, ribbons, and the like. Shapes of electroactive elements 26 may be configured for a variety of properties including, but not limited to, surface area, and the like. In some examples, electroactive elements 26 may have a width less than about 0.5 mm, such as about 0.025 mm to about 0.5 mm, where the width is measured in a direction perpendicular to a length of the electroactive elements. In some examples, the width represents a diameter of electroactive elements 26 having a circular cross-sectional shape. In some examples, electroactive elements 26 may have a length greater than about five millimeters, where a length is measured from one longitudinal end to another longitudinal end. In some examples, one or more electroactive elements have substantially a round cross-section or substantially a flat cross-section. For example, electroactive elements used for navigation may have a length between 5 mm and 5 cm, while electroactive elements used for stiffness may have a length between about 5 cm and about 25 cm.

Electroactive elements 26 may have a variety of sizes (e.g., diameters, circumferences, lengths, widths, shapes, etc.). In some examples, all electroactive elements 26 may have a same size (e.g., may only differ by manufacturing variances). In some examples, electroactive elements 26 may have different sizes and/or shapes. For example, distal portion 20 may include a first size or shape of electroactive elements 26 that is more suited for steering distal portion 20, while proximal portion 18 may include a second size or shape of electroactive elements 26 that is more suited for stiffening proximal portion 18. In some examples, a size and distribution of electroactive elements 26 may be selected according to a particular density of electroactive elements 26 on elongated body 16. For example, a number of electroactive elements 26 and volume of each electroactive element 26 may be selected so that electroactive elements 26 may occupy a percentage of volume of distal portion 20 or proximal portion 18 of elongated body 16, such as between about 1% and about 10%.

In some examples, electroactive elements 26 may have a median largest dimension (e.g., length, width, diameter) that is less than about 25 cm, such as in a range of about 5 cm to about 25 cm. For example, an ability of each electroactive element 26 to dissipate heat may be related to a surface area of the respective electroactive elements 26, such that a larger size of electroactive elements 26 for a particular total volume of electroactive elements 26 may have a greater ability to dissipate heat. In some examples, electroactive elements 26 include between 4 electroactive elements and 100 electroactive elements. In some examples, electroactive elements 26 may have a relatively small size. For example, smaller sizes may have a faster cooling time and may be arranged non-linear configurations to maximize an effect equivalent to a bigger size. In this way, heat dissipation time may be reduced, such as no longer than 5-10 seconds, as faster heat dissipation may allow faster recycling.

Electroactive elements 26 may be distributed about elongated body 16 (e.g., in the longitudinal direction and/or in a circumferential direction) in a variety of configurations. For example, electroactive elements 26 may be distributed in such a way that selective contraction of one or more electroactive elements 26 creates a desired shape, stiffness property, or dimension of elongated body 16. In some examples, electroactive elements 26 may be staggered at different axial positions along longitudinal axis 22 of elongated body 16. For example, as shown in FIG. 1B, electroactive element 26A is positioned at a first axial position along longitudinal axis 22 and electroactive element 26B is positioned at a second axial position along longitudinal axis 22. By positioning electroactive elements 26 at different axial positions, elongated body 16 may be configured to form different shapes that incorporate a plurality of bends. While only two axial positions are shown, distal portion 20 and/or proximal portion 18 may include electroactive elements distributed at more than two axial positions, such five, ten, twenty, or more axial positions. In some examples, a size or density of electroactive elements may vary according to an axial distribution. For example, a density of electroactive elements may increase or decrease along a distal direction.

Figure 1C:
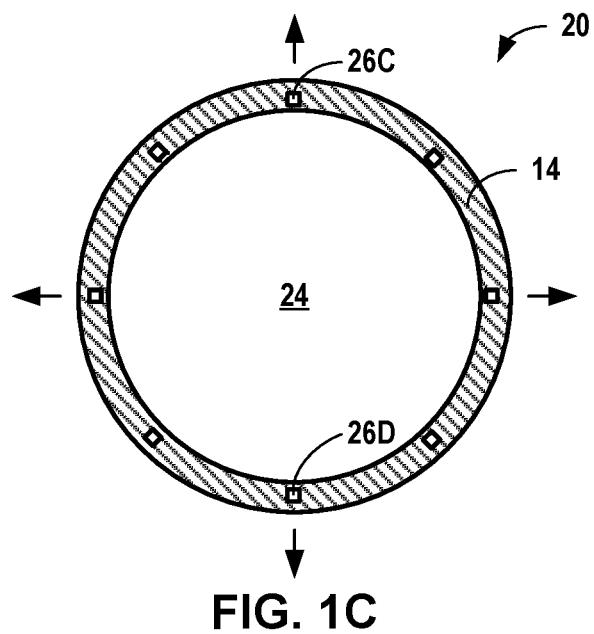
FIG. 1C is a schematic axial cross-sectional diagram illustrating example the catheter of FIG. 1A.

In some examples, electroactive elements 26 may be staggered around elongated body 16, e.g., circumferentially distributed in the case of distal portion 20 and/or proximal portion 18 having a circular cross-section (the cross-section being taken in a direction orthogonal to longitudinal axis 22 of elongated body 16). FIG. 1C is a schematic axial cross-sectional diagram illustrating example catheter 12 of FIG. 1A. As shown in FIG. 1C, electroactive element 26C is positioned at a first circumferential or radial position and electroactive element 26D is positioned at a second circumferential or radial position, opposite electroactive element 26C. By positioning electroactive elements 26 at different circumferential or radial positions, elongated body 16 may be configured to form bends in a variety of directions from longitudinal axis 22.

In some examples, two or more electroactive elements 26 or sets of electroactive elements 26 may be arranged in opposing configurations. In some examples, two or more electroactive elements 26 or sets of electroactive elements 26 may be diametrically opposed (positioned at substantially 180° from one another). For example, in FIG. 1C, electroactive element 26C is diametrically opposed to electroactive element 26D. As such, a difference in an electrical signal strength between electroactive element 26C and electroactive element 26D may be configured to bend distal portion 20 toward a corresponding one of electroactive element 26C or electroactive element 26D. In other examples, three or more electroactive elements 26 or sets of electroactive elements 26 may be symmetrically opposed (positioned at substantially 120° from one another), or arranged in another configuration of electroactive elements 26 positioned at multiple planes of symmetry. In each of these examples, the electroactive elements that are diametrically opposed or otherwise symmetrically opposed may be coextensive and/or coterminous with each other along longitudinal axis 22 or may have different lengths measured along the longitudinal axis.

In some examples, a position and/or size of electroactive elements 26 may be relatively even or constant according to a circumferential or radial distribution of electroactive elements 26 around distal portion 20 and/or proximal portion 18. For example, an even distribution of electroactive elements 26 may increase a minimum distance between adjacent electroactive elements 26, such that a heat distribution may be relatively even. In some examples, a position and/or size of electroactive elements 26 may vary according to a circumferential or radial distribution of electroactive elements 26 around distal portion 20 and/or proximal portion 18. For example, variation in spacing of electroactive elements 26 may provide distal portion 20 and/or proximal portion 18 with asymmetrical properties or actuation.

In some examples, one or more electroactive elements 26 are staggered in a spiral arrangement around the elongated body and along longitudinal axis 22 of elongated body 16. For example, electroactive elements 26 be positioned at different axial and circumferential positions, such that elongated body 16 may form a variety of shapes. In some examples, electroactive elements 26 staggered in a spiral arrangement may have a more even dissipation of thermal energy. For example, electroactive elements 26 staggered in a spiral arrangement may be spaced such that electroactive elements 26 may have a greater spacing from adjacent electroactive elements for a particular density of electroactive elements 26 than arrangements in which only an axial position or a circumferential position of electroactive elements is varied.

While not shown, in some examples, proximal portion 18 of catheter 12 may include one or more alignment elements (e.g., markers visible to a clinician without the aid of a medical imaging device) configured to indicate a predetermined position of distal tip 14 relative to the patient. For example, a first predetermined position of distal tip 14 may correspond to a particular location in vasculature of a patient that may benefit from various shapes, dimensions, or properties of distal portion 20 and/or proximal portion 18.

Figure 1D:
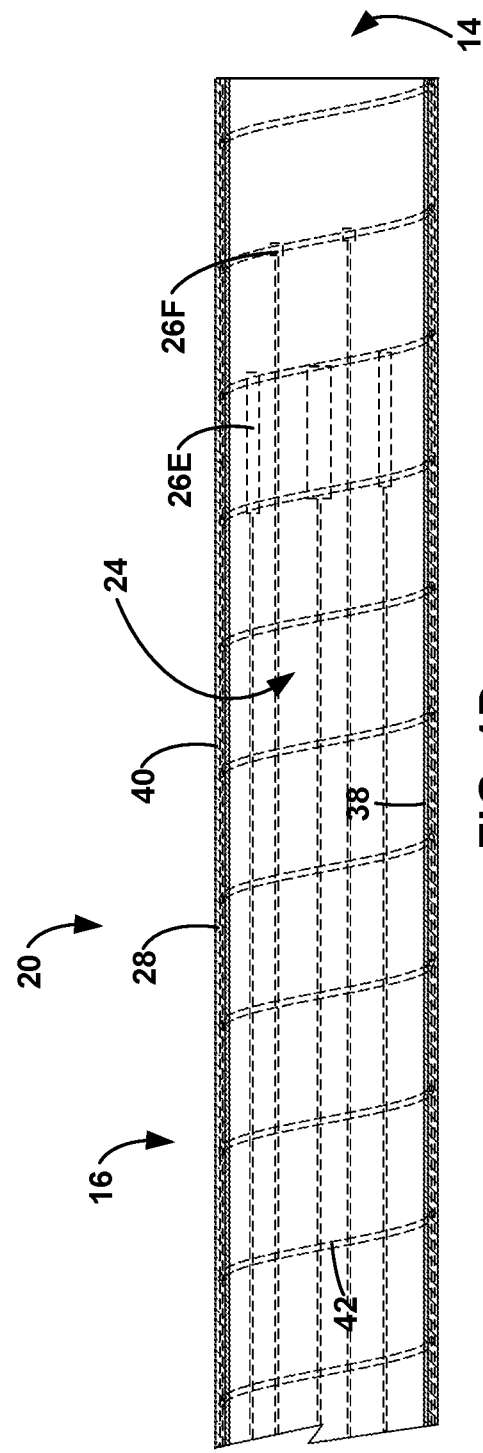
FIG. 1D is a schematic longitudinal cross-sectional diagram illustrating an example catheter.

In some examples, electroactive elements discussed herein may be incorporated into catheters that utilize structural support members. FIG. 1D is a schematic longitudinal cross-sectional diagram illustrating example catheter 12. In the example of FIG. 1D, elongated body 16 further comprises an inner liner 38, an outer jacket 40, and a structural support member 42 positioned between at least a portion of inner liner 38 and at least a portion of the outer jacket 40.

In some examples, one or more portions of inner liner 38 may be lubricious to facilitate the introduction and passage of a medical device, particulates such as pieces of a clot/thrombus, a therapeutic agent, or the like, through inner lumen 24. In some examples, the material from which portions of inner liner 38 is formed may itself be lubricious (e.g., polytetrafluoroethylene (PTFE)). For example, a lubricious inner surface that may allow relatively easy movement of a guidewire, particulates, and/or fluid through inner lumen 24. In addition to, or instead of, being formed from a lubricious material, in some examples, an inner surface of inner liner 38 may be coated with a lubricious coating such as a hydrophilic coating. The inner surface may be formed from any suitable material including, but not limited to, PTFE, expanded PTFE a fluoropolymer, perfluoroalkyoxy alkane (PFA), fluorinated ethylene propylene (FEP), polyolefin elastomer, and the like.

In some examples, one or more portions of an inner surface of inner liner 38 may be configured to have a relatively high affinity to a clot material by, for example, using a suitable surface treatment (e.g., a coating and/or etching) on inner liner 38 to promote mechanical or chemical engagement with the clot. (Such affinity may be measured, for example, with a DMA (dynamic mechanical analyzer) equipped with a shear sandwich clamp.) For example, the inner surface of distal portion 20 may be treated with a surface coating, etching, or other roughening mechanism, so that the distal section better engages with the clot, such that the inner surface of the distal section may be configured to promote at least one of mechanical or chemical clot engagement. A roughened or less lubricious surface of an inner surface that is brought in contact with the clot may allow for the clot to stick better to the inner surface, which may allow the clot to be pulled into catheter 12 more effectively. Examples of suitable coating materials to increase the affinity of the clot to an inner surface of inner liner 38 may include, for example, a thermoplastic elastomer such as ChronoPrene™ (AdvanSource Biomaterials, Wilmington, Mass.); a polyolefin elastomer such as ethylene-octene or ethylene-butene copolymer, or the like.

Elongated body 16 also includes outer jacket 40 positioned over structural support member 42 and inner liner 38, the structural support member 42 being positioned between portions of inner liner 38 and outer jacket 40. In some examples, outer jacket 40 may be positioned around structural support member 42 such that outer jacket 40 covers at least a part or all of both inner liner 38 and structural support member 42. Outer jacket 40, together with inner liner 38 and structural support member 42, may be configured to define elongated body 16 having the desired structural characteristics (e.g., flexibility, kink resistance, torque responsiveness, structural integrity, pushability, and column strength, which may be a measure of a maximum compressive load that can be applied to elongated body 16 without taking a permanent set). For example, outer jacket 40 may have stiffness characteristics that contribute to the desired stiffness profile of elongated body 16.

Elongated body 16 includes one or more structural support members 42 positioned over inner liner 38. Structural support member 42 is configured to increase the structural integrity of elongated body 16 while allowing elongated body 16 to remain relatively flexible. For example, structural support member 42 may be configured to help elongated body 16 substantially maintain its cross-sectional shape (e.g., circular or nearly circular) or at least help prevent elongated body 16 from buckling or kinking as it is navigated through tortuous anatomy. Additionally, or alternatively, structural support member 42, together with inner liner 38, and outer jacket 40, may help distribute both pushing and rotational forces along a length of elongated body 16, which may help prevent kinking of elongated body 16 upon rotation of elongated body 16 or help prevent buckling of elongated body 16 upon application of a pushing force to elongated body 16. As a result, a clinician may apply pushing forces, rotational forces, or both, to the proximal portion of elongated body 16, and such forces may cause a distal portion of elongated body 16 to advance distally, rotate, or both, respectively.

Structural support member 42 may include one or more tubular braided structures, one or more coil members defining a plurality of turns, e.g., in the shape of a helix, or a combination of a braided structure and a coil member. Structural support member 42 can be made from any suitable material, such as, but not limited to, a metal (e.g., a nickel titanium alloy, stainless steel, tungsten, titanium, gold, platinum, palladium, tantalum, silver, or a nickel-chromium alloy, a cobalt-chromium alloy, or the like), a polymer, a fiber, or any combination thereof. In some examples, structural support member 42 may include one or more metal wires braided or coiled around inner liner 38. The metal wires may include round wires, flat-round wires, flat wires, or any combination thereof.

In some examples, structural support member 42 may include one or more materials configured as electroactive elements 26. For example, structural support member 42 may comprise one or more materials configured to contract in response to an electrical signal. Such a electroactive structural support member may be positioned at distal portion 20 of catheter 12, at proximal portion 18, or both proximal and distal portions 18, 20. In response to an electrical signal, the electroactive structural support member may be configured to decrease in length, such as by reducing the pitch of a coiled structural support member or reducing the size of the spacing in a braided structural support member. In examples in which distal portion 20 includes the electroactive structural support member, the heating of the electroactive structural support member in response to an electrical signal may proximally retract distal tip 14, e.g., to stiffen distal portion 20. In examples in which proximal portion 18 includes the electroactive structural support member, the heating of the electroactive support member in response to an electrical signal may retract distal tip 14, e.g., to stiffen or straighten proximal portion 18.

In some examples, electroactive elements 26 are separate from structural support member 42 but in thermal contact with at least a portion of structural support member 42, which may provide one or more advantages. For example, electroactive elements 26 contract in response to thermal energy created by an electrical signal. Once the electrical signal is no longer applied to the respective electroactive element 26, the thermal energy may be dissipated from electroactive element 26. The faster this thermal energy may be dissipated, the less strain may be created on the respective electroactive element and/or the faster the electroactive element may be cycled. Cycling of an electroactive element may include, for example, delivering an electrical signal to the electroactive element to cause it to heat up and contract and then subsequently cooling the electroactive element to cause it to return to a baseline state in which is no longer contracted as a result of the delivered electrical signal. By disposing one or more electroactive elements 26 in thermal contact with structural support member 42, thermal energy from electroactive elements 26 may be more quickly dissipated.

In some examples, such as illustrated in the example of FIG. 1D, structural support member 42 may be a coiled structural support member. In this example, electroactive elements 26 may be configured to reduce a coil pitch of the coiled structural support member in response to the application of the electrical signal. For example, electroactive elements 26 positioned on a first side of the coiled structural support member may be configured to contract to reduce a coil pitch on the first side of the coiled structural support member and increase, refrain from decreasing, or decrease to a lesser extent a coil pitch on an opposite side of the coiled support member to deflect distal tip 14.

In some examples, one or more electroactive elements 26 are separate from structural support member 42 and are distributed between adjacent turns of the coiled structural support member 42. In the example of FIG. 1D, electroactive element 26E is positioned between (e.g., connecting) two adjacent turns of the coiled structural support member. In response to receiving an electrical signal, electroactive element 26E may be configured to contract and reduce a coil pitch between the two adjacent turns of the coil. In these examples, the one or more electroactive elements 26 may be employed with a continuous or discontinuous coil, which may have a consistent pitch or a varying pitch in an "at rest" state of catheter 12 (e.g., before an electrical signal has been applied to electroactive elements 26 and when electroactive elements 26 are not in a heated state). By positioning electroactive elements between structural support member 42, catheter 12 may have faster length contraction and stiffness profile adjustment during navigation. For example, a distal section of catheter 12 beyond an arch may require more proximal support to push it further up into the vasculature. For navigation into vessels and past the arch, electroactive elements 26 positioned between structural support member 42 may amplify the bending of distal tip 14, thereby allowing achievement of a greater angle of bend in catheter 12 than otherwise possible.

Referring back to FIGS. 1A and 1B, in some examples, catheter control system 10 may be configured to control a shape or dimension of elongated body 16 by receiving user selections corresponding to shapes or dimensions of elongated body 16 or specific anatomical structures and generating control signals based on the user selections. Thus, in some examples, catheter control system 10 may include a user interface 34, control circuitry 35, a memory 36, and an electrical signal generation circuitry 37. Control circuitry 35 is configured to receive user input via user interface 34, the user input indicating a user selection of a particular shape or dimension of elongated body 16 or a particular anatomical structure, which may correspond to a particular shape or dimension of elongated body 16 stored as data in memory 36.

The particular shape or dimension of elongated body 16 may correspond to a dimension or shape created through contraction of electroactive elements 26. User interface 34 may include any suitable input mechanism including, but not limited to, a keyboard, buttons, a peripheral pointing device, a touch screen, and any other device that may be used to receive user inputs and/or display selection outputs. User interface 34 may be configured to send the user selection to control circuitry 35.

Control circuitry 35 is operably connected to and configured to access information from memory 36 and to control electrical signal generation circuitry 37. Components described as control circuitry 35 and other controllers or processors herein may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. In general, control system 10 may comprise any suitable arrangement of hardware (e.g., circuitry), alone or in combination with software and/or firmware, to perform the various techniques described herein attributed to control system 10.

In some examples, memory 36 may store information associating different predetermined catheter shapes or dimensions with the combination of electroactive elements 26 to which an electrical signal should be delivered to achieve the respective shape and/or dimension, and, in some examples, the specific electrical signal that should be delivered to the respective electroactive element 26 to achieve the desired shape or dimension. The specific electrical signal can be characterized by, for example, the one or more electrical signal parameter values of the electrical signal, such as, but not limited to, a current amplitude, power, and/or duration with which the electrical signal is delivered to the electroactive element.

In addition to or instead of the predetermined catheter shapes or dimensions, in some examples, memory 36 may store information associating one or more predetermined anatomical structures (e.g., the MCA or carotid siphon) or medical procedures (e.g., aspiration) with the combination of electroactive elements 26 to which an electrical signal should be delivered to configure elongated body 16 to be navigated within or through the anatomical structure or to facilitate the medical procedure, and, in some examples, the specific electrical signal that should be delivered to the respective electroactive element 26 to achieve the desired shape or dimension of elongated body for the associated anatomical structure or medical procedure.

Memory 36 may also store operating instructions for execution by control circuitry 35. Memory 36 may include separate memories for storing data that may benefit from separate physical memory modules.

Memory 36 may comprise any suitable memory, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Although control circuitry 35 and memory 36 are described as separate modules, in some examples, control circuitry 35 and memory 36 may be physically and/or functionally integrated.

Control circuitry 35 may be configured to receive the user selection from user interface 34 and control electrical signal generation circuitry to generate, based on the user selection, a control signal. The control signal may include one or more electrical signals configured to contract one or more electroactive elements 26 to generate a shape, dimension, or other configuration corresponding to the user selection in memory 36. Electrical signal generation circuitry 37 may be configured to send the control signal to the one or more electroactive elements 26. In some examples, a current supplied by electrical signal generation circuitry 37 may be proportional in magnitude and/or time applied to a degree of deflection of distal tip 14. For example, electrical signal generation circuitry 37 may supply a particular current for a particular amount of time to electroactive elements 26.

In some examples, catheter 12 and catheter control system 10 may be configured to bend distal tip 14 away from longitudinal axis 22. For example, catheter 12 may include electroactive elements 26 arranged (e.g. staggered) along longitudinal axis 22 of elongated body 16, as illustrated in FIG. 1C. Catheter control system 10 may be configured to send a control signal that causes electroactive element 26C to contract to a greater extent than electroactive element 26D, such as by applying a stronger electrical signal to electroactive element 26C. As a result, distal portion 20 may bend to the right in a direction of electroactive element 26C away from longitudinal axis 22.

In some examples, catheter 12 and catheter control system 10 may be configured to offset distal tip 14 from longitudinal axis 22. For example, catheter 12 may include electroactive elements 26 staggered along longitudinal axis 22 of elongated body 16, as illustrated in FIG. 1B. Catheter control system 10 may be configured to send a control signal that causes both electroactive element 26A and electroactive element 26B to contract, such as by applying electrical signals to both electroactive element 26A and electroactive element 26B. As a result, distal portion 20 may form an S-shape having two curves.

In some examples, catheter 12 and catheter control system 10 may be configured to retract distal tip 14 along longitudinal axis 22. For example, catheter 12 may include electroactive elements 26 diametrically opposed, as illustrated electroactive elements 26c and 26D in FIG. 1C. In this example, catheter control system 10 may be configured to send a control signal that causes both electroactive element 26C and electroactive element 26D to contract substantially equally along longitudinal axis 22, such as by applying substantially equal electrical signals to both electroactive element 26C and electroactive element 26D. As a result, distal portion 20 and/or proximal portion 18 may retract and stiffen.

In some examples, catheter 12 and catheter control system 10 may be configured to selectively activate a portion of the one or more electroactive elements 26, such that not all electroactive elements 26 in catheter 12 may be simultaneously activated. For example, to stiffen catheter 12, control circuitry 35 may be configured to at least or only activate more electroactive elements 26 that are more proximally located in catheter 12. As another example, to bend distal tip 14 of catheter 12, control circuitry 35 may be configured to at least or only active electroactive elements 26 that near distal tip 14 of catheter 12.

In some examples, catheter 12 may include one or more protection devices and/or systems configured to limit heat generated within catheter 12. In some examples, catheter 12 includes one or more temperature sensors configured to detect a temperature measurement of the one or more electroactive elements 26 and/or an area proximate to the one or more electroactive elements 26. The temperature sensors can be, for example, integrally formed with one or more electroactive elements 26 or positioned within elongated body 16 close to the one or more electroactive elements 26 to sense an increase in temperature resulting from delivery of an electrical signal to the one or more electroactive elements 26. Control circuitry 35 may be configured to receive the temperature measurement from the one or more temperature sensors, determine that the temperature measurement exceeds a temperature threshold corresponding to safe operation of catheter 12, and limit an amount of current from electrical signal generation circuitry based on the temperature measurement exceeding the temperature threshold. In some examples, electrical signal generation circuitry 37 may include a rheostat configured to limit an amount of current to electroactive elements 26 based on a current threshold of the rheostat.

Figure 2A:
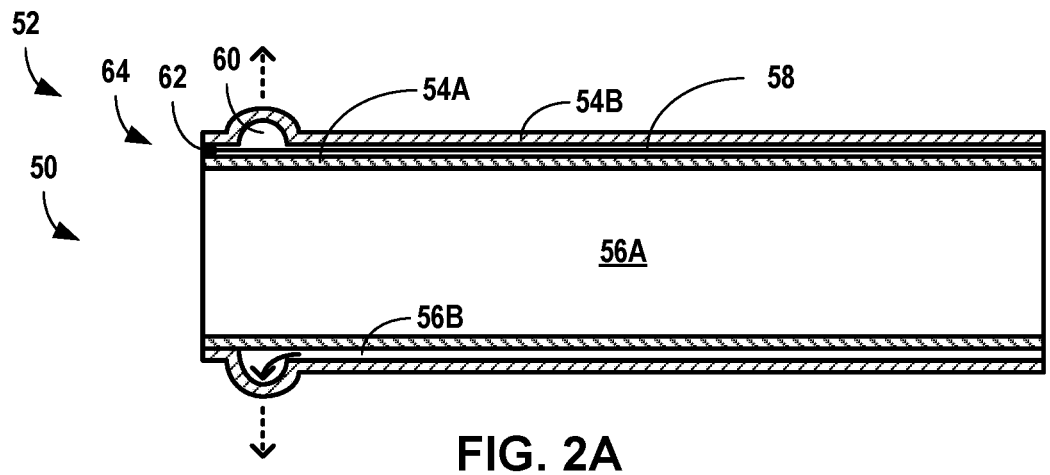
FIG. 2A is a schematic longitudinal cross-sectional diagram illustrating an example catheter that includes an expandable structure in an expanded position.
Figure 2B:
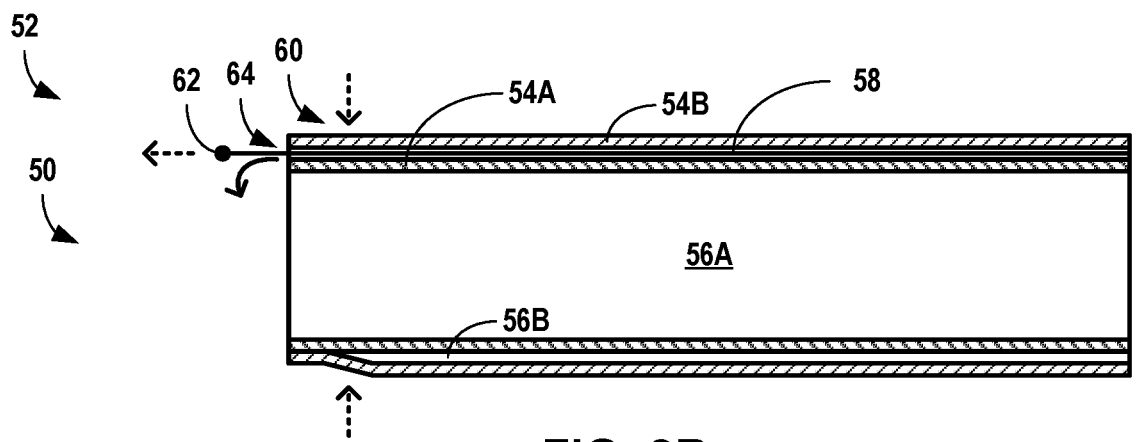
FIG. 2B is a schematic longitudinal cross-sectional diagram illustrating an example catheter that includes an expandable structure in a contracted position.

In some examples, electroactive elements discussed herein may be incorporated into catheters for use in applications other than navigation. FIGS. 2A and 2B are schematic longitudinal cross-sectional diagrams illustrating a distal portion 52 of an example catheter 50 that includes an expandable structure 60 configured to expand and contract based on actuation of an electroactive element 58. Catheter 50 includes an inner elongated body 54A and an outer elongated body 54B. Inner elongated body 54A defines an inner lumen 56A and outer elongated body 54B defines an outer lumen 56B. Outer lumen 56B terminates a discharge opening 64, which can be used to purge air from outer lumen 56B, as well as release an inflation fluid from outer lumen 56B. Properties of catheter 50, such as composition of elongated bodies 56 and electroactive element 58, may be similar to properties of catheter 12 discussed in FIGS. 1A-1D.

Outer elongated body 54B may include one or more expandable structures 60 (e.g., one or more balloons) configured to receive fluid through outer lumen 56B, expand in response to receiving the fluid, discharge fluid through a discharge opening 64, and contract in response to discharging the fluid. Outer lumen 56B may be configured to receive fluid into expandable structure 60 from a proximal portion of catheter 50. For example, saline or other fluid may be injected through outer lumen 24B to inflate expandable structure 60. At distal portion 52, outer elongated body 54B contacts inner elongated body 54A except for discharge opening 64. While catheter 50 may be described with respect to inner elongated body 54A and outer elongated body 54B, in other examples, a single elongated body that includes inner lumen 56A and an inflation lumen corresponding to outer lumen 56B may be used. The inflation lumen may or may not have a radial cross-section and can be, for example, only along one side of inner lumen 56A in some examples. Electroactive element 58 may be coupled to a plug 62. Plug 62 may be configured to retract into discharge opening 64 in response to the application of the electrical signal to electroactive element 58 to seal discharge opening 64.

FIG. 2A is a schematic longitudinal cross-sectional diagram illustrating expandable structure 60 in an expanded position. When current is applied to electroactive element 58, electroactive element 58 contracts proximally and pulls plug 62 into discharge opening 64 to seal fluid into expandable structure 60 and maintain pressure in expandable structure 60. Fluid may be provided through outer lumen 56B into expandable structure 60 to expand (e.g., inflate) expandable structure 60.

FIG. 2B is a schematic longitudinal cross-sectional diagram illustrating expandable structure 60 in a contracted position. When current is no longer applied to electroactive element 58, electroactive element 58 may expand and distally push plug 62 out of discharge opening 64 to unseal fluid from expandable structure 60 and contract (e.g., deflate) expandable structure 60. Fluid may then discharge from expandable structure 60 through discharge opening 64 into vasculature of a patient. In this way, expandable structure 60, in combination with electroactive element 58, may be quickly inflated and deflated. Plug 62 and/or discharge opening 64 may have a variety of shapes including, but not limited to, elliptical, round, square, and the like.

FIGS. 3A-3E illustrate various shapes and changes in dimensions for distal portions of catheters discussed herein. While shown as individual shapes, any combination of shapes and characteristics of shapes (e.g., angles, dimensions, relative positions, etc.) may be created by distributing electroactive elements in various configurations and contracting the distributed electroactive elements in various selections. Additionally or alternatively, any of the shapes or characteristics of shapes may apply to a proximal portion of the catheters.

Figure 3A:
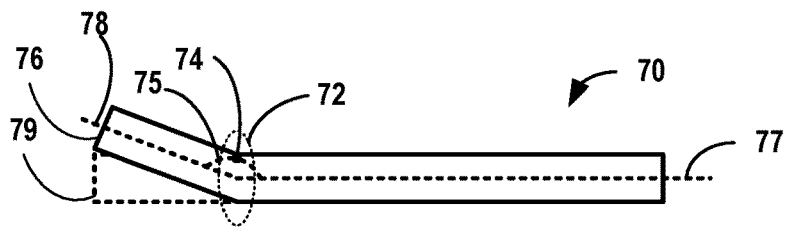
FIG. 3A is a schematic side view diagram illustrating an example catheter having a deflected shape caused by contraction of an electroactive element.

FIG. 3A is a schematic side view diagram illustrating a distal portion 70 of an example catheter having a deflected shape caused by contraction of an electroactive element 74. Electroactive element 74 is configured to contract, in response to receiving the electrical signal, and bend a portion of distal portion 70 in a direction away from a longitudinal axis 77. The contraction of electroactive element 74 may cause deflection of a distal tip 76 from a previous position 79 away from longitudinal axis 77 of the catheter. As such, distal tip 76 may form an axis of deflection 78 from a point of deflection 72 of the catheter. Axis of deflection 78 may form a deflection angle 75 with longitudinal axis 77 of the catheter. In some examples, deflection angle 75 may have a maximum angle greater than about 20°.

Figure 3B:
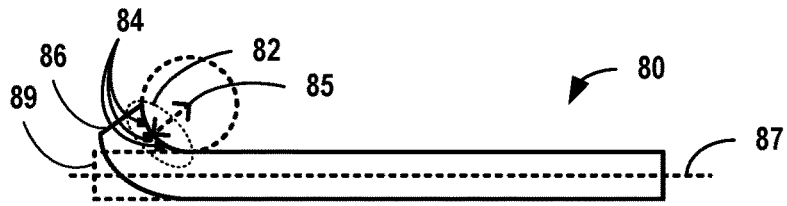
FIG. 3B is a schematic side view diagram illustrating an example catheter having a bended shape caused by contraction of a plurality of electroactive elements.

FIG. 3B is a schematic side view diagram illustrating a distal portion 80 of an example catheter having a bended shape caused by contraction of a plurality of electroactive elements 84. The plurality of electroactive elements 84 is configured to contract, in response to receiving electrical signals, and form a curved portion 82 of distal portion 80 in a direction away from a longitudinal axis 87. The contraction of the plurality of electroactive elements 84 may cause gradual deflection of a distal tip 86 from a previous position 89 away from longitudinal axis 87 of the catheter. As such, distal tip 86 may form a radius of curvature 85 of curved portion 82 of distal portion 80 of the catheter. In some examples, radius of curvature 85 may have a maximum radius of curvature greater than about 10 cm.

Figure 3C:
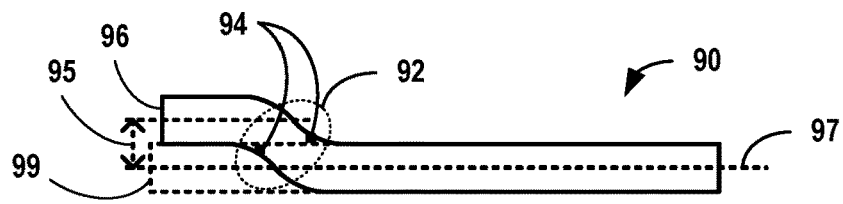
FIG. 3C is a schematic side view diagram illustrating an example catheter having an offset shape caused by contraction of a plurality of electroactive elements.

FIG. 3C is a schematic side view diagram illustrating a distal portion 90 of an example catheter having an offset shape caused by contraction of a plurality of electroactive elements 94. The plurality of electroactive elements 94 is configured to contract, in response to receiving electrical signals, and curve a first portion of distal portion 90 in a first direction away from a longitudinal axis 97 at a first axial position and a second portion of distal portion 90 in a second direction toward longitudinal 97 axis at a second axial position. The contraction of the plurality of electroactive elements 94 may cause two different deflections of a distal tip 96 from a previous position 99 away from and toward, respectively, longitudinal axis 97 of the catheter to form an "S" shape. As such, distal tip 96 may have an offset 92 from longitudinal axis 97. In some example, offset 92 may have a maximum offset distance 95 greater than about 0.5 cm. While illustrated in FIG. 3C as an "S" shape offset, an offset of a distal tip may be caused by a variety of shapes, such as the shapes illustrated in FIGS. 3A and 3B. For example, distal tip 76 may have an offset distance from the longitudinal axis caused by deflection angle 75.

Figure 3D:
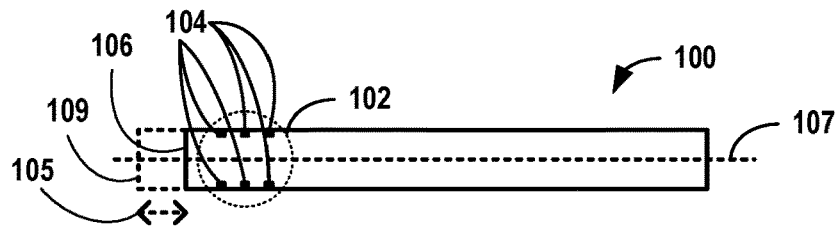
FIG. 3D is a schematic side view diagram illustrating an example catheter having a retracted shape caused by contraction of a plurality of electroactive elements.

FIG. 3D is a schematic side view diagram illustrating distal portion 100 of an example catheter having a straight and/or retracted shape caused by contraction of a plurality of electroactive elements 104. The plurality of electroactive elements 104 is configured to contract, in response to receiving electrical signals, and draw distal tip 106 from a previous position 109 in a proximal direction along a longitudinal axis 107 to stiffen distal portion 100. The contraction of the plurality of electroactive elements 104 may cause retraction 102 on opposing sides of distal portion 100. As such, distal portion 100 may have a shorter length and/or more rigid structure. For example, instead of bending to navigate through tortuous vasculature, a stiffened, retracted, and/or straightened distal portion caused diametrically opposed electroactive elements of the plurality of electroactive elements 104 may enable a fluid, such as aspiration fluid, to more easily flow through an inner lumen of the catheter. In some examples, retraction 102 may have a maximum retraction length 105 greater than about 2% than a total axial length (length of electroactive elements of the plurality of electroactive element 104 on each side of distal portion 100 along longitudinal axis 107) of the plurality of electroactive elements 104.

Figure 3E:
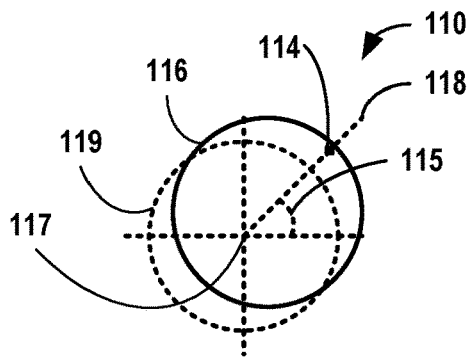
FIG. 3E is a schematic front view diagram illustrating an example catheter having a bended shape cause by contraction of an electroactive element.

FIG. 3E is a schematic front view diagram illustrating a distal portion 110 of an example catheter having a bended shape caused by contraction of an electroactive element 114. Electroactive element 114 is configured to contract, in response to receiving the electrical signal, and bend distal portion 110 in a direction away from the longitudinal axis. The contraction of electroactive element 114 may cause deflection of a distal tip 116 from a previous position 119 away from longitudinal axis 117 of the catheter. As such, distal tip 116 may have a direction of deflection 118 from a point of deflection of the catheter. Direction of deflection 118 may form a radial angle 115 with the longitudinal axis of the catheter. In some examples, radial angle 115 may have a range of angles from 0 through 360. For example, a plurality of electroactive elements may be configured to contract simultaneously, such that relative strengths of electrical signals between the plurality of electroactive elements may be selected for a variety of radial angles.

Figure 4:
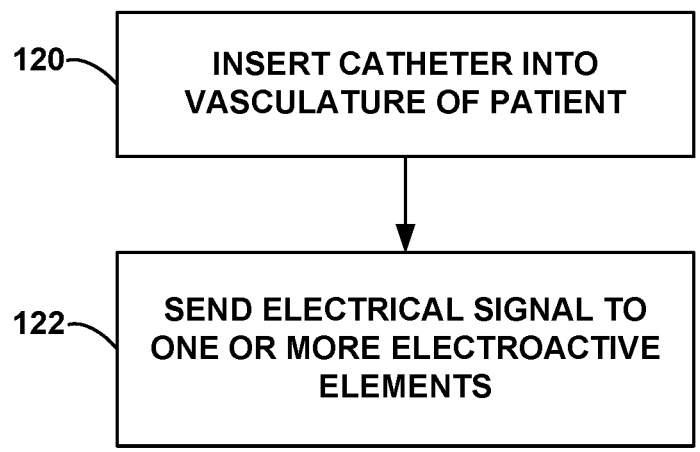
FIG. 4 is a flow diagram of an example method of using a catheter.

FIG. 4 is a flow diagram of an example method of using a catheter that includes one or more electroactive elements configured to contract in response to an application of an electrical signal. The technique of FIG. 4 includes a clinician inserting catheter 12 into vasculature of a patient (120). After insertion of catheter 12, a clinician may control catheter control system 10 to send an electrical signal to one or more electroactive elements 26 to contract one or more electroactive elements 26 (122). In some examples, the electrical signal has a current less than about 100 milliamps. The contraction of one or more electroactive elements 26 is configured to change a dimension or a shape of elongated body 16. For example, to bend distal portion 20 of elongated body 16 in a first direction away from longitudinal axis 22 of elongated body 16, catheter control system 10 may apply an electrical signal to electroactive element 26A to contract electroactive element 26A along longitudinal axis 22 of elongated body 16. As another example, to stiffen distal portion 20 of catheter 12 along longitudinal axis 22, catheter control system 10 may apply an electric signal to electroactive elements 26A and 26B, which are substantially diametrically opposed, to contract electroactive elements 26A and 26B along longitudinal axis 22 of elongated body 16.

The techniques of FIG. 4 may be performed one or more times throughout a procedure. For example, a vasculature of a patient may include a first vessel location having a low degree bend in a first direction, a second vessel location having a high degree bend in a second direction, and a third vessel location corresponding to a procedural site. In this example, a clinician may advance catheter 12 to the first vessel location while in a default configuration (e.g., while electroactive elements 26 are in a baseline state in which they have are not contracted) and control catheter control system 10 to send an electrical signal to a first set of electroactive elements 26 to produce a first configuration of distal portion 20 for navigating the low degree bend in the first direction. The clinician may advance distal tip 14 through the first vessel location and control catheter control system 10 to return catheter 12 to the default configuration. The clinician may then advance catheter 12 to the second vessel location and control catheter control system 10 to send an electrical signal to a second set of electroactive elements 26 to produce a second configuration of distal portion 20 for navigating the high degree bend in the second direction. The clinician may advance distal tip 14 through the second vessel location and control catheter control system 10 to return distal portion 20 to the default configuration. The clinician may then advance catheter 12 to the third vessel location and control catheter control system 10 to send an electrical signal to a third set of electroactive elements to produce a third configuration of distal portion 20 for maintaining or increasing fluid flow through catheter 12 to the procedural site. In this way, the techniques of FIG. 4 may be used to navigate and position catheter 12 for a variety of procedures and in a variety of vasculatures.

In addition or alternative to navigation, the technique of FIG. 4 may be used to expand and contract an expandable structure of a catheter, such as expandable structure 60 of catheter 50 of FIGS. 2A and 2B. The technique of FIG. 4 includes a clinician inserting catheter 50 into vasculature of a patient (120). Prior to or after insertion of catheter 50, a clinician may control a catheter control system, such as catheter control system 10, to send an electrical signal to one or more electroactive elements 58 to contract one or more electroactive elements 58 (122). The contraction of one or more electroactive elements 58 is configured to seal discharge opening 64 with plug 62. For example, to contract electroactive element 58 proximally and pull plug 62 into discharge opening 54, catheter control system 10 may apply an electrical signal to electroactive element 58 to contract electroactive element 58 along a longitudinal axis of catheter 50. Fluid may be provided through outer lumen 56B into expandable structure 60 to expand (e.g., inflate) expandable structure 60. The expansion of one or more electroactive elements 58 is configured to unseal discharge opening 64 with plug 62. For example, to expand electroactive element 58 distally and push plug 62 out of discharge opening 64, catheter control system 10 may reduce or no longer apply the electrical signal to electroactive element 58 to expand electroactive element 58 along the longitudinal axis of catheter 50. Fluid may then discharge from expandable structure 60 through discharge opening 64 into the vasculature of the patient.

Figure 5:
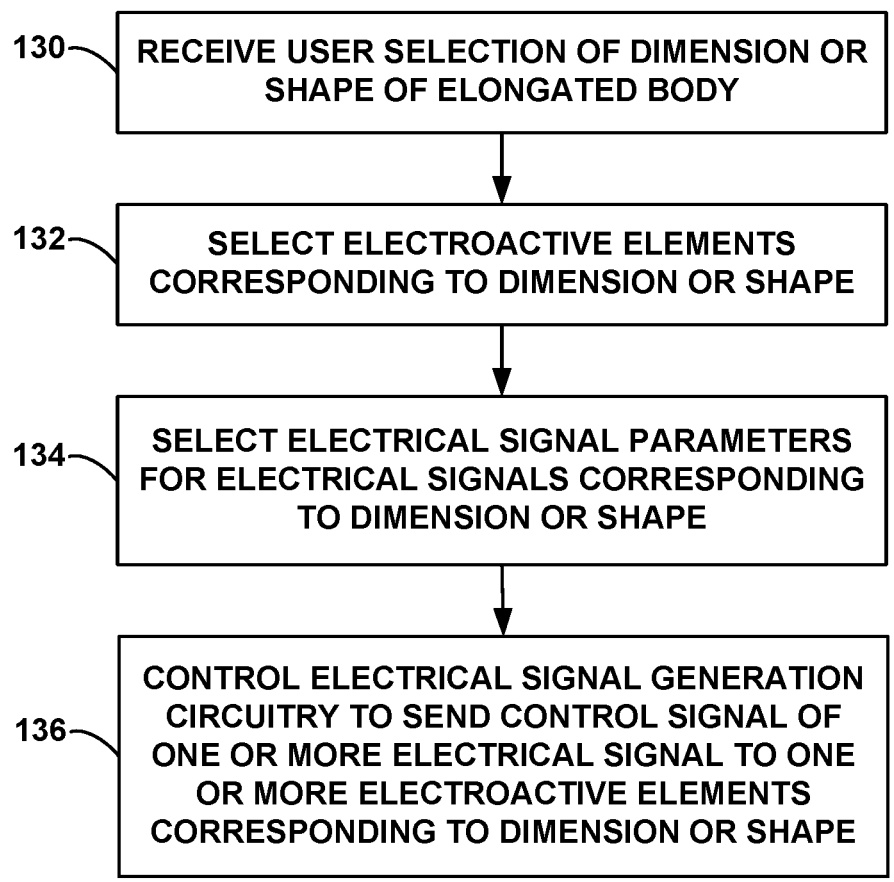
FIG. 5 is a flow diagram of an example method of controlling a shape or dimension of a catheter.

FIG. 5 is a flow diagram of an example method of controlling a shape or dimension of a catheter that includes electroactive elements configured to contract in response to a user selection of a particular dimension or shape of an elongated body of a catheter. While FIG. 5 is described with respect to catheter control system 10, in other examples, the technique of FIG. 5 may be used with other catheter control systems or devices configured in other ways.

In accordance with the technique shown in FIG. 5, control circuitry 35 receives, via user interface 34, a user selection of a particular dimension or shape of elongated body 16 of catheter 12 or a particular anatomical structure (130). In response to receiving the user input, control circuitry 35 selects one or more electroactive elements 26 that, when heated, will change a dimension or a shape of elongated body 16 to correspond to the user-selected shape, dimension, and/or anatomical structure (132). For example, control circuitry 35 may reference memory 36 and determine which one or more electroactive elements 26 and respective electrical signals (e.g., electrical signal parameter values, such as current amplitude) correspond to the user-selected shape, dimension, and/or anatomical structure (134). Thereafter, control circuitry 35 may control electrical signal generation circuitry 37 to generate and send a control signal to one or more electroactive elements 26 corresponding to the user-selected shape, dimension, and/or anatomical structure (136). The control signal includes one or more electrical signals configured to contract one or more electroactive elements 26 to form the dimension or shape of the elongated body.

Figure 6:
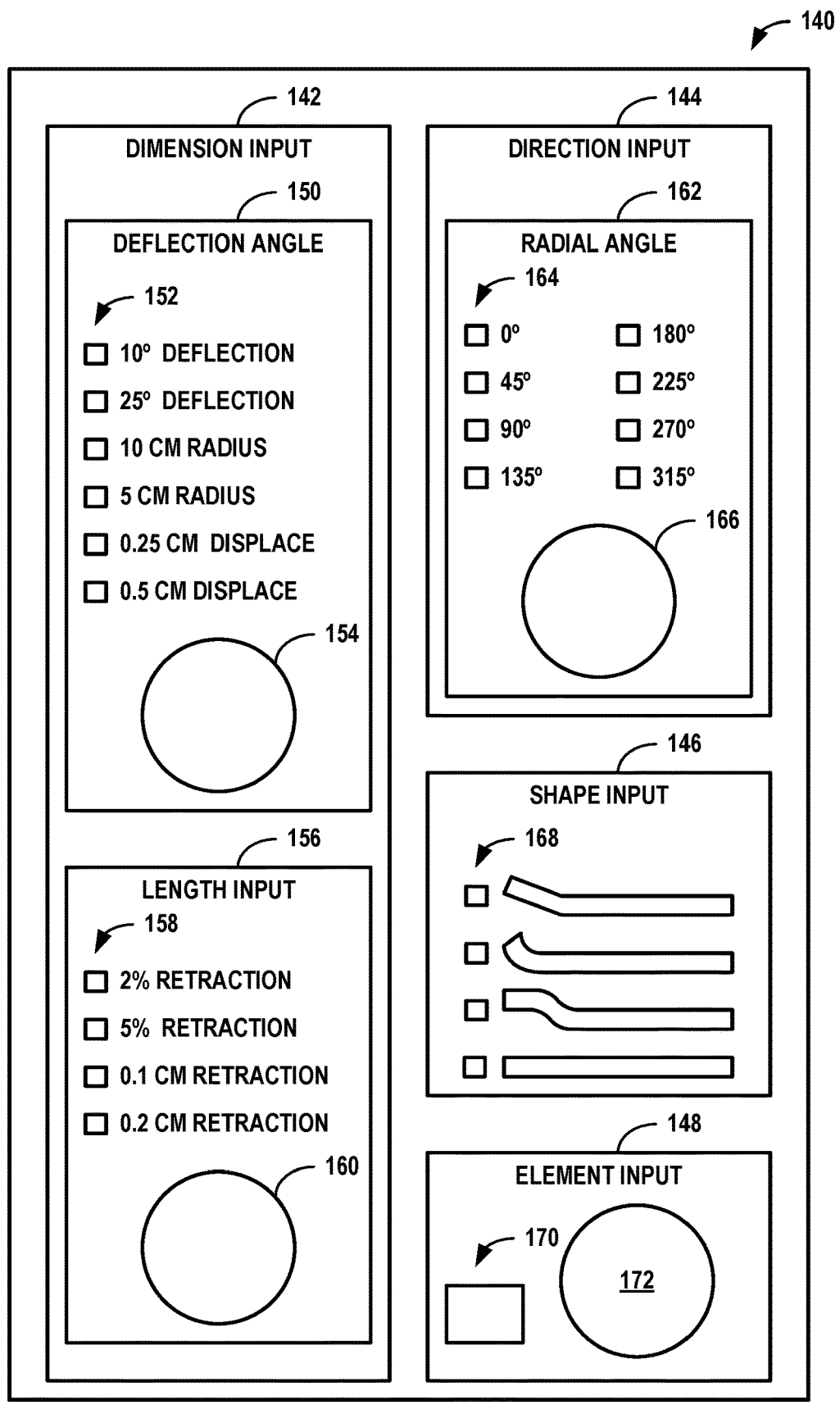
FIG. 6 is a diagram illustrating an example user interface for controlling a shape or dimension of a catheter.

FIG. 6 is a diagram illustrating an example user interface 140 for controlling a shape or dimension of a catheter that includes electroactive elements configured to contract in response to receiving an electrical signal. User interface 140 is an example of a graphical user interface that control circuitry 35 may generate and present via a display device of user interface 34 (FIG. 1B). In general, user interface 140 may present one or more user-selectable options for controlling a shape and/or dimension of catheter 12. In response to receiving user input via user interface 140, control circuitry 35 may determine which of the one or more electroactive elements 26 and, in some cases, the respective electrical signals (e.g., electrical signal parameter values, such as current amplitude), correspond to the user-selected shape, dimension, and/or anatomical structure and then control electrical signal generation circuitry 37 to generate and deliver an electrical signal to the selected one or more electroactive elements 26, as discussed with respect to FIG. 5.

In the example shown in FIG. 6, user interface 140 includes a dimension input 142, a direction input 144, a shape input 146, and an element input 148. In other examples, user interface 140 may only include a subset of one or more the inputs 142-148, or different types of inputs.

Via dimension input 142, control circuitry 35 may be configured to receive a user selection corresponding to one or more dimensions of distal portion 20 and/or proximal portion 18 of catheter 12. Dimensions input 142 may include a deflection angle input 150 and a length input 156. Via deflection angle input 150, control circuitry 35 may be configured to receive a user selection corresponding to an extent of deflection of distal tip 14. Deflection angle input 150 may include preselected inputs 152 that include deflection angles (e.g., "10 DEFLECTION" and "25 DEFLECTION"), radii of curvature (e.g., "10 CM RADIUS" and "5 CM RADIUS"), and/or offset of distal tip 14 (e.g., "0.25 CM DISPLACE" and "0.5 CM DISPLACE"). In some examples, deflection angle input 150 may also include a manual deflection input 154 corresponding to manual control of deflection of distal tip 14, such as by manually increasing a strength of one or more electrical signals to selected electroactive elements 26.

Via length input 156, control circuitry 35 may be configured to receive a user selection corresponding to an extent retraction of distal tip 14. Length input 156 may include preselected input 158 that include percent retraction ("2% RETRACTION" and "5% RETRACTION") and length retraction ("0.1 CM RETRACTION" and "0.2 CM RETRACTION"). In some examples, length input 156 may also include a manual length input 160 corresponding to manual control of length of distal portion 20 and/or proximal portion 18, such as by manually increasing a strength of one or more electrical signals to selected electroactive elements 26.

Via direction input 144, control circuitry 35 may be configured to receive a user selection corresponding to one or more directions of distal portion 20 and/or proximal portion 18 of catheter 12. For example, direction input 144 may include a radial angle input 162. Radial angle input 162 may be configured to receive a user selection corresponding to a direction of deflection of distal tip 14. Radial angle input 162 may include preselected input 164 that include preselected radial angles (e.g., "0°," "45°," "90°," "135°," "180°," "225°," "270°," and "315°"). In some examples, radial angle input 162 may also include a manual direction input 166 corresponding to manual control of direction of distal tip 14, such as by manually selecting a radial angle corresponding to selection of certain electroactive elements 26.

Via shape input 146, control circuitry 35 may be configured to receive a user selection corresponding to one or more shapes of distal portion 20 and/or proximal portion 18 of catheter 12. Shape input 146 may include preselected inputs 168 that include various shapes of distal portion 20 and/or proximal portion 18.

Via element input 148, control circuitry 35 may be configured to receive a user selection corresponding to one or more elements of distal portion 20 and/or proximal portion 18 of catheter 12. Element input 148 may include an element selection input 170 for selecting a particular electroactive element 26 or group of electroactive elements 26. In some examples, element input 148 may also include a manual contraction input 172 corresponding to a degree of contraction of the selected electroactive element 26 or group of electroactive elements 26, such as by manually adjusting a strength of an electrical signal for the selected electroactive element 26 or group of electroactive elements 26.

Various aspects of the disclosure have been described. These and other aspects are within the scope of the following claims.

What is claimed is:

1. A catheter, comprising:
an elongated body including a proximal portion and a distal portion, the elongated body comprising a structural support member configured to provide longitudinal support to the elongated body; and
one or more electroactive elements in at least one of the proximal portion or the distal portion of the elongated body, the one or more electroactive elements each comprising a contractive material configured to contract in response to a temperature change generated by an application of an electrical signal to the respective electroactive element, the contraction of the contractive material of the one or more electroactive elements being configured to change a dimension or a shape of the elongated body,
wherein at least one of the one or more electroactive elements is in thermal contact with at least a portion of the structural support member to dissipate heat generated by the application of the electrical signal, and
wherein a heat dissipation time of the at least one electroactive element from a contracted phase during the application of the electrical signal, and back to an expanded phase after the application of the electrical signal is less than about 10 seconds.

2. The catheter of claim 1, wherein the one or more electroactive elements are disposed at a distal tip of the catheter, the distal tip being at a distal end of the distal portion.

3. The catheter of claim 1,
wherein the catheter comprises two or more electroactive elements, and
wherein the two or more electroactive elements are staggered around the elongated body in a direction orthogonal to a longitudinal axis of the elongated body.

4. The catheter of claim 1,
wherein the catheter comprises two or more electroactive elements, and
wherein the two or more electroactive elements are staggered along a longitudinal axis of the elongated body.

5. The catheter of claim 1, wherein the one or more electroactive elements are in a spiral arrangement around the elongated body and along a longitudinal axis of the elongated body.

6. The catheter of claim 1, wherein the elongated body further comprises:
an inner liner; and
an outer jacket,
wherein the one or more electroactive elements and the structural support member is positioned between at least a portion of the inner liner and at least a portion of the outer jacket.

7. The catheter of claim 1, wherein the structural support member is a coiled structural support member.

8. The catheter of claim 1, wherein the one or more electroactive elements comprise at least two electroactive elements that are substantially diametrically opposed.

9. The catheter of claim 1, wherein each of the one or more electroactive elements is configured to contract between about 2% and about 8% to the contracted phase when heated above a transition temperature of the contractive material of the respective electroactive element.

10. The catheter of claim 1, wherein each of the one or more electroactive elements is configured to contract between about 2% and about 8% along a longitudinal axis of the catheter.

11. The catheter of claim 1, wherein the contractive material comprises a nickel titanium (NiTi) alloy having a Ni:Ti composition range between about 40:60 and about 60:40.

12. The catheter of claim 1, wherein the one or more electroactive elements have an electrical resistivity greater than about 30 micro-ohms·centimeter.

13. The catheter of claim 1, wherein the elongated body comprises one or more electrical conductors electrically coupled to the one or more electroactive elements, the one or more electroactive elements being configured to receive the electrical signal via an electrical conductor of the one or more electrical conductors.

14. The catheter of claim 1, wherein a first electroactive element of the one or more electroactive elements is configured to contract, in response to receiving the electrical signal, and bend the at least one of the proximal portion or the distal portion of the elongated body in a first direction away from a longitudinal axis of the elongated body.

15. The catheter of claim 1, wherein a first electroactive element and a second electroactive element of the one or more electroactive elements are configured to contract, in response to receiving the electrical signal, and stiffen the at least one of the proximal portion or the distal portion of the elongated body.

16. The catheter of claim 1,
wherein the elongated body further comprises an expandable structure and defines a lumen in fluid communication with the expandable structure, the lumen terminating in a discharge opening, and
wherein at least one of the one or more electroactive elements is coupled to a plug and configured to retract the plug relative to a distal end of the elongated body to seal the discharge opening in response to the application of the electrical signal.

17. The catheter of claim 1,
wherein the contacted phase corresponds to contraction of at least about 2% of the at least one electroactive element, and
wherein the expanded phase corresponds to about 0% contraction of the at least one electroactive element.

18. The catheter of claim 2, wherein the one or more electroactive elements are disposed about 2 centimeters or less from the distal tip of the catheter.

19. The catheter of claim 7, wherein the one or more electroactive elements are configured to reduce a coil pitch of the coiled structural support member in response to the application of the electrical signal.

20. The catheter of claim 7, wherein the one or more electroactive elements are distributed between turns of the coiled structural support member.

21. The catheter of claim 11, wherein the nickel titanium alloy comprises a Ni:Ti composition of about 50:50.

22. A catheter, comprising:
an elongated body including a proximal portion and a distal portion, the elongated body comprising a structural support member configured to provide longitudinal support to the elongated body; and
one or more electroactive elements in at least one of the proximal portion or the distal portion of the elongated body, the one or more electroactive elements each being configured contract in response to a temperature change generated by an application of an electrical signal to the respective electroactive element, the contraction of the one or more electroactive elements being configured to change a dimension or a shape of the elongated body, the one or more electroactive elements comprising a nickel titanium (NiTi) alloy having a Ni:Ti composition of about 50:50,
wherein at least one of the one or more electroactive elements is in thermal contact with at least a portion of the structural support member to dissipate heat generated by the application of the electrical signal, and
wherein a heat dissipation time of the at least one electroactive element from a contracted phase during the application of the electrical signal, and back to an expanded phase after the application of the electrical signal is less than about 10 seconds.

23. The catheter of claim 22, wherein the one or more electroactive elements have an electrical resistivity less than about 50 micro-ohms·centimeter.

24. The catheter of claim 22, wherein the elongated body further comprises one or more electrical conductors electrically coupled to the one or more electroactive elements, the one or more electroactive elements being configured to receive the electrical signal via an electrical conductor of the one or more electrical conductors.

* * * * *